US006183498B1

(12) United States Patent
Devore et al.

(10) Patent No.: US 6,183,498 B1
(45) Date of Patent: Feb. 6, 2001

(54) METHODS AND PRODUCTS FOR SEALING A FLUID LEAK IN A TISSUE

(76) Inventors: Dale P. Devore, 3 Warwick Dr., Chelmsford, MA (US) 01824; Charles Putnam, 11 Woodview Dr., Belle Meade, NJ (US) 08502; James M. Pachence, 18 Elm St., Hopewell, NJ (US) 08525

( * ) Notice: Under 35 U.S.C. 154(b), the term of this patent shall be extended for 0 days.

(21) Appl. No.: 09/180,687

(22) Filed: Sep. 20, 1999

(51) Int. Cl.$^7$ ............................ A61B 17/04; A61K 38/17
(52) U.S. Cl. ...................... 606/214; 530/356; 530/402; 530/408
(58) Field of Search .................... 606/213, 214; 623/6; 530/356, 402, 408, 410

(56) References Cited

U.S. PATENT DOCUMENTS

| | | | |
|---|---|---|---|
| 3,438,374 | 4/1969 | Falb et al. | 606/214 |
| 3,453,222 | 7/1969 | Young | 260/8 |
| 3,515,551 | 6/1970 | Audran et al. | 96/35 |
| 4,215,200 | 7/1980 | Miyata et al. | 106/155 |
| 4,233,360 | 11/1980 | Luck et al. | 428/310 |
| 4,264,155 | 4/1981 | Miyata et al. | 106/155 |
| 4,264,493 | 4/1981 | Battista | 260/117 |
| 4,349,470 | 9/1982 | Battista | 260/117 |
| 4,388,428 | 6/1983 | Kuzma et al. | 523/106 |
| 4,407,787 | 10/1983 | Stemberger | 424/28 |
| 4,427,808 | 1/1984 | Stol et al. | 524/24 |
| 4,451,568 | 5/1984 | Schneider et al. | 623/66 |
| 4,452,925 | 6/1984 | Kuzma et al. | 523/106 |
| 4,453,939 | 6/1984 | Zimmerman et al. | 604/368 |
| 4,488,911 | 12/1984 | Luck et al. | 106/161 |
| 4,563,490 | 1/1986 | Stol et al. | 524/24 |
| 4,565,580 | 1/1986 | Miyata et al. | 106/124 |
| 4,581,030 | 4/1986 | Bruns et al. | 623/5 |
| 4,606,910 | 8/1986 | Sawyer | 424/28 |
| 4,650,616 | 3/1987 | Wajs | 264/2.6 |
| 4,713,446 | 12/1987 | DeVore et al. | 530/356 |
| 4,789,663 | 12/1988 | Wallace et al. | 514/21 |
| 4,839,345 | 6/1989 | Doi et al. | 514/21 |
| 4,950,699 | 8/1990 | Holman | 524/21 |
| 4,969,912 | 11/1990 | Kelman et al. | 623/66 |
| 5,024,742 | 6/1991 | Nesburn et al. | 204/157.68 |
| 5,067,961 | 11/1991 | Kelman et al. | 623/5 |
| 5,112,350 | 5/1992 | Civevchia et al. | 606/107 |
| 5,147,514 | 9/1992 | Mechanic | 204/157.68 |
| 5,156,613 | 10/1992 | Sawyer | 606/214 |
| 5,173,295 | 12/1992 | Wehling | 424/94.67 |
| 5,190,057 | 3/1993 | Sarfarazi | 604/294 |
| 5,209,776 | 5/1993 | Bass et al. | 606/214 |
| 5,219,895 | 6/1993 | Kelman | 522/68 |
| 5,279,825 | 1/1994 | Wehling | 424/94.67 |
| 5,290,552 | 3/1994 | Sierra | 424/94.64 |
| 5,292,362 | 3/1994 | Bass et al. | 106/124 |
| 5,294,314 | 3/1994 | Nesburn et al. | 204/157.68 |
| 5,352,715 | 10/1994 | Wallace et al. | 523/115 |
| 5,354,336 | 10/1994 | Kelman et al. | 623/6 |
| 5,356,614 | 10/1994 | Sharma | 424/45 |
| 5,412,076 | 5/1995 | Gagnieu | 530/356 |
| 5,431,790 | 7/1995 | Nesburn et al. | 204/157.68 |
| 5,441,491 | 8/1995 | Verschoor et al. | 603/304 |
| 5,690,675 | 11/1997 | Sawyer et al. | 606/229 |

FOREIGN PATENT DOCUMENTS

| | | |
|---|---|---|
| 0 244 688 A2 | 11/1987 | (EP) . |
| 0 330 344 A2 | 8/1989 | (EP) . |
| 466 383 A1 | 1/1992 | (EP) . |
| WO83/00339 | 2/1983 | (WO) . |
| WO92/13025 | 8/1992 | (WO) . |
| WO94/21306 | 9/1994 | (WO) . |
| 0 191 994 A1 | 2/1996 | (WO) . |
| WO96/03159A1 | 2/1996 | (WO) . |
| PCT/US97/08124 | 10/1997 | (WO) . |

OTHER PUBLICATIONS

Shimizu, et al., "Studies on copolymers of Collagen and a Synthetic Polymer," Biomat., Med. Dev. Art. Org., 5(1): 49–66 (1977).

Shimizu, et al., "Studies on Copolymers of Collagen and a Synthetic Polymer," Biomat., Biomat., Med. Dev. Art. Org., 6(4): 375–391 (1978).

Lloyd, et al., "Covalent Bonding of Collagen and Acrylic Polymers," In Biomedical and Dental Applications of Polymers, C.G. Goblein et al. (eds.), Plenum Press (1980) pp. 59–84.

Stenzel, et al.,"Collagen as a Biomaterial," 231–53 (1974).

Galligan, et al. "Polyurethanes," Chapter 16, pp. 255–267.*

Buonocore, "Bonding to Hard Dental Tissues,"Chapter 15, pp. 225–254.*

Lee, Jr. et al., "Surface Preparation and Various Adhesive Resins, "Chapter 17, pp. 269–289.*

De Toledo et al., "Preliminary Evaluation of a New Collagen–Derived Bioadhesive," Arvo Annual Meeting Abstract Issue, Investigative Opthalmology and Visual Science, 31: 317–Abstract No. 1556–14 (1990).*

Scott et al., "Fibrin Tissue Adhesive in Sealing Conjunctival Wound Leaks, "Arvo Annual Meeting Abstract Issue, Investigative Opthalmology and Visual science, 31: 87 Abstract No. 431 (1990).*

(List continued on next page.)

Primary Examiner—Gary Jackson
(74) Attorney, Agent, or Firm—Testa, Hurwitz & Thibeault, LLP

(57) ABSTRACT

Methods and products for rapidly sealing a fluid leak in a tissue are provided. A polymerizable protein is applied to a tissue having an opening which creates a fluid leak in the tissue, in order to seal the opening. The tissue area and opening coated with the polymerizable protein are exposed to an initiator in order to polymerize the covering in situ, and create a seal over the opening that prevents fluid leakage. The methods and products to the invention may be used, for example, to seal airholes in lung injuries and to seal anastomoses and suture lines for blood vessels.

16 Claims, No Drawings

OTHER PUBLICATIONS

Kram et al., "Splenic Salvage Using Biologic Glue,"Arch Surgery, 119:1309–1311 (1984).*

Scheele et al., "Splenic Repair by Fibrin Tissue Adhesive and Collagen Fleece," Surgery, 95: 6–13 (1982).*

Siedentop et al., "Experimental Use of Fibrin Tissue Adhesive In Middle Ear Surgery," Laryngoscope, 93: 1310–1313 (1983).*

Epstein et al., "A New Autologous Fibrinogen–Based Adhesive for Otologic Surgery,"Annals of Otology, Rhinology & Laryngology, 95 (1): 40–45 (1986).*

Fisher, "Collagen Goes Beyond the Cosmetic,"The New York times, Jan. 29, 1991.*

Science Watch, "Finding a Natural Glue,"The New York Times, 1991.*

Braunwald, "Evaluation of Crosslinked Gelatin as a Tissue Adhesive and Hemostatic Agent: An Experimental Study," Surgery, 59(6): 1024–1030 (1966).*

Snyder et al., "An Improved 2, 4, 6–Trinitrobenezene-sulfonic Method for the Determination of Amines, " Analytical Biochemistry, 64: 284–288 (1975).*

Aldrich Chemical Company Brochure, p. 1102 (1999).*

* cited by examiner

METHODS AND PRODUCTS FOR SEALING A FLUID LEAK IN A TISSUE

BACKGROUND OF THE INVENTION

The ability to establish bonding between biological tissues has long been a goal of biomedical researchers. Attempts to provide desired adhesion through mechanical bonding have proven to be neither convenient nor permanent. For this reason, much attention was devoted to developing synthetic polymers as biomedical adhesives. Such materials, however, have been observed to induce inflammatory tissue reactions. Moreover, the ability of these materials to establish permanent bonding under physiological conditions has not been fully realized.

The known toxicity associated with synthetic adhesives has led investigations towards a development of biologically derived adhesives as bonding materials. Among such adhesives, fibrin based glues have commanded considerable attention. Commercial fibrin tissue adhesives are derived from human plasma and, therefore, pose potential health risks such as adverse immunogenic reactions and transmission of infectious agents. Moreover, the bond strength imparted by such adhesives is relatively weak compared to collagen adhesives.

Collagen, the major connective tissue protein in animals, possesses numerous characteristics not seen in synthetic polymers. Characteristics of collagen often cited include good compatibility with living tissue, promotion of cell growth, and absorption and assimilation of implantations. Natural collagen fibers, however, are not very useful in their native form due to intermolecular crosslinking, insolubility, rigid triple-helical structure, and immunogenicity.

Various methods and materials have been proposed for modifying collagen to render it more suitable as a biomedical adhesive. "In many instances, the prior modified collagen-based adhesives suffer from various deficiencies which include crosslinking/polymerization reactions that generate exothermic heat, long reaction times, and reactions that are inoperative in the presence of oxygen and physiological pH ranges. Moreover, many of the prior art modified collagen-based adhesives contain toxic materials, hence rendering them unsuitable for biomedical use."

Another problem with collagen and other protein-based adhesives is the ability to form bond strengths and film strengths sufficient for the various uses to which such adhesives may be applicable. For example, U.S. Pat. No. 3,438,374 discloses a general matrix as a bioadhesive. Although the material was useful in some applications, the material did not work very well or failed in applications where the material was subjected to substantial pressures or was used to fill a substantial gap in tissue (as opposed to adhering two pieces of tissue together). For example, the adhesive was found not to be effective in sealing divided bronchial stumps (which is characterized by large gaps in tissue) and also was not effective in sealing blood vessels (which involve elevated fluid flow at high pressures).

A more recent advance in the field is the use of collagen monomers derivatized with an acylating agent or a sulphonating agent and polymerized with an appropriate polymerization initiator such as a chemical oxidant, ultraviolet irradiation, a suitable oxidative enzyme or atmospheric oxygen. These materials were shown to be biologically compatible, and their use was proposed for a number of biological applications. In particular, it was disclosed that these materials be used as adhesives to hold two tissues together or to hold a synthetic lenticule to an eye. They also were disclosed as useful in the formation of flexible films which could be used as a lap following surgery to prevent adhesion, as a synthetic tympanic membrane, as a substitute facial tissue, and as a wound dressing component. It was stated that the adhesive also may be used to seal an incision following cataract removal. The material was not proposed for use in sealing fluid leaks in a tissue that is a conduit and in particular in a tissue that is exposed to pulsating and elevated pressures in situ.

SUMMARY OF THE INVENTION

The invention provides methods and products for sealing a fluid leak in a tissue. The various methods and products permit one or more of the following advantages: (1) the ability to seal quickly, in some instances under 30 seconds; (2) the ability to be immediately exposed to elevated pressures of at least 50 mm Hg, and in some instances, above 125 and even above 250 mm Hg; (3) the ability to be immediately exposed to pulsating fluid upon sealing, particularly at high pressures; (4) the ability to plug substantial gaps in tissue, as opposed to adhesively binding tissues in contact with one another, to one another; and (5) the ability to seal body fluids in bodily conduits.

According to one aspect of the invention, a method for sealing a fluid leak in a tissue is provided. A polymerizable protein is applied to the tissue to form a covering for an opening in the tissue, which opening creates a fluid leak in the tissue. The covering then is exposed to a initiator so as to polymerize the covering in situ, so as to attach the covering to the tissue and so as to seal the opening from fluid leakage. The invention is useful in connection with sealing anastomoses and suture lines for blood vessels. The invention also is useful for sealing airholes in lung injuries, including injuries to parenchymal and bronchiole tissue (especially bronchiole stumps). The foregoing are examples of tissues that act as conduits for fluid which pulses through the conduits at elevated pressures. The invention also is useful in connection with sealing leakage in the bladder, repairing leakage in the bowel, and repairing leaks in dura mater.

According to some embodiments of the invention, the polymerization can be carried out in less than 3 minutes. In certain embodiments, the polymerization preferably is carried out in less than 30 seconds, more preferably between about 10 and 30 seconds and most preferably in about 15 seconds.

In other embodiments, the polymerizable protein is a viscous fluid, and the polymerization is carried out at between a pH of 6.0–9.0, more preferably 7.8–8.8, and most preferably between about 8.2 and 8.5. In still other embodiments, the polymerizable protein is in a solvent which includes an initiator. In these embodiments, the initiator can be sodium persulfate, sodium thiosulfate, ferrouschloride tetrahydrate, sodium bisulfate or an oxidative enzyme. Most preferably the initiator is sodium persulfate, and the sodium persulfate is present in the solvent collagen mixture in a range of 0.01M to 0.2M. Preferably, the initiator is a photochemical initiator. It is preferred that the irradiation used to initiate polymerization is a light band having a wavelength between about 250 and 550 nm.

In certain embodiments, the polymerizable protein is selected from the group consisting of collagen, albumin, gelatin, elastin, and fibrinogen. In certain embodiments the protein is derivatized with an agent that enhances the solubility of the protein under physiological conditions. In preferred embodiments, the polymerizable protein is collagen derivatized with an acylating agent and/or a sulfonating agent.

In other embodiments the method also includes the step of applying a primer to the tissue surface prior to applying the polymerizable protein to the tissue. The primer enhances the strength of the tissue seal. In a preferred embodiment the primer is a dilute solution of collagen having a concentration of 1–10 mg/ml. In a preferred embodiment the concentration of the dilute collagen solution is 4–8 mg/ml. In another embodiment the primer has a pH of 6.0–9.0. In a preferred embodiment the pH is 8.2–8.5.

According to another aspect of the invention, a method for sealing a fluid leak in a tissue is provided. A primer is applied to the tissue to form a primer layer and then a polymerizable protein is applied to the primer layer to form a covering for an opening in the tissue, which opening creates a fluid leak in the tissue. The covering then is exposed to a initiator so as to polymerize the covering in situ, so as to attach the covering to the tissue and so as to seal the opening from fluid leakage.

According to some embodiments of the invention, the polymerization can be carried out in less than 3 minutes. In certain embodiments, the polymerization preferably is carried out in less than 30 seconds, more preferably between about 10 and 30 seconds and most preferably in about 15 seconds.

In other embodiments, the polymerizable protein is a viscous fluid, and the polymerization is carried out at between a pH of 6.0–9.0, more preferably 7.8–8.8, and most preferably between about 8.2 and 8.5. In still other embodiments, the polymerizable protein is in a solvent which includes an initiator. In these embodiments, the initiator can be sodium persulfate, sodium thiosulfate, ferrouschloride tetrahydrate, sodium bisulfate or an oxidative enzyme. Most preferably the initiator is sodium persulfate, and the sodium persulfate is present in the solvent collagen mixture in a range of 0.01M to 0.2M. Preferably, the initiator is a photochemical initiator. It is preferred that the irradiation used to initiate polymerization is a light band having a wavelength between about 250 and 550 nm.

In certain embodiments, the polymerizable protein is selected from the group consisting of collagen, albumin, gelatin, elastin, and fibrinogen. In certain embodiments the protein is derivatized with an agent that enhances the solubility of the protein under physiological conditions. In preferred embodiments, the polymerizable protein is collagen derivatized with an acylating agent and/or a sulfonating agent.

In other embodiments the primer is a dilute solution of collagen having a concentration of 1–10 mg/ml. In a preferred embodiment the concentration of the dilute collagen solution is 4–8 mg/ml. In another embodiment the primer has a pH of 6.0–9.0. In a preferred embodiment the pH is 8.2–8.5.

According to another aspect of the invention, a biosealant is provided. The biosealant is a polymerizable protein containing an initiator in an amount so that the polymerizable protein can be polymerized in less than 30 seconds when exposed to an appropriate light source.

According to another aspect of the invention, another biosealant is provided. This biosealant is a polymerizable protein containing an initiator and that can be light polymerized in less than 3 minutes and that after exposure to light for between 15 and 180 seconds, withstands at least 300 mm Hg when applied to and polymerized upon a blood vessel.

According to another aspect of the invention, still another biosealant is provided. This biosealant is a polymerizable protein in a solvent containing an acylating initiator in an amount of at least 0.1M, and preferably between about 0.05M and 0.2M sodium persulfate.

According to another aspect of the invention a primer is provided. The primer is an adhesive protein in a dilute solution. Preferably the adhesive protein is collagen and the collagen is diluted in a solution of 0.1 M phosphate buffer at a concentration of 1–10 mg/ml. In a preferred embodiment the concentration of the dilute collagen solution is 4–8 mg/ml. In another embodiment the primer has a pH of 6.0–9.0. In a preferred embodiment the pH is 8.2–8.5.

The invention also includes kits which include two or more of any of the foregoing elements of the tissue sealing compositions of the invention. For example, derivatized collagen may be provided in one container and sodium persulfate can be provided in another container, both present in amounts whereby upon mixing, a polymerizable protein useful according to the invention is provided. As another example, both the derivatized protein and the sodium persulfate could be provided as lyophilized preparations in one or more containers, and a solvent in another container whereby the polymerizable protein solutions of the invention can be reconstituted upon mixing. As an additional example, a protein derivatized with an agent that results in the collagen being soluble under physiological conditions can be supplied in one container and an initiator such as sodium persulfate in a buffered solution can be provided in another container, wherein the materials are present in relative amounts such that when mixed according to the instructions the sodium persulfate is present in an amount of between 0.05M and 0.2M and the final pH of the mixture is between 8.2 and 8.5. Optionally the kit may also include a primer in a syringe or other container.

According to another aspect of the invention, a method for sealing tissue leaks is provided. The method involves the steps of applying a primer to the tissue and applying a protein based adhesive on top of the primer. Preferably, the primer is a dilute solution of collagen. In one embodiment the protein based adhesive is a polymerizable protein and the method further includes the step of exposing the polymerizable protein to an initiator in situ to polymerize the proteins. In another embodiment, the protein based adhesive is selected from the group consisting of fibrin glue and modified collagen based adhesives.

As will be understood by those of ordinary skill in the art, any one of the foregoing features or elements of the invention may be combined with any one or more of the other features and elements of the invention, all of which are intended to be embraced by the present disclosure. These and other aspects of the invention will be described in more detail below.

DETAILED DESCRIPTION OF THE INVENTION

The invention involves the use of polymerizable proteins. The proteins useful in the invention include collagen, albumin, gelatin, elastin and fibrinogen. The foregoing materials, particularly when prepared according to the preferred embodiments of the invention, are biologically compatible.

As employed herein, the term "biologically compatible" refers to polymerizable protein and polymerized products which are incorporated or implanted into or placed adjacent to the biological tissue of a subject and, more particularly, remain intact for a sufficient period of time to permit healing and do not induce an immune response or deleterious tissue reaction after such incorporation or implantation or placement. The protein may be derived from virtually any source, including purified from natural sources, produced recombinately, etc.

The polymerizable protein is applied to tissues in situ to form a covering over an opening which creates a fluid leak in the tissue. The tissue includes vascular tissue, lung tissue, bladder tissue, bowel tissue and dura mater. In preferred embodiments, the tissue is a soft tissue within the body, not normally exposed, and which is subjected to pulsating fluid pressures such as vascular tissue and lung tissue. In other preferred embodiments, the tissue is characterized by an opening that forms a substantial gap.

For vascular arteries, the pressure of the blood on the artery is about 120 mm Hg in a normal individual. This may be higher or lower, depending upon the individual and the circumstances of the individual. When a vascular artery requires a seal resulting from a suture line or an anastomosis, it is believed that the seal must be capable of withstanding about 250 mm Hg pressure. Upon forming the seal, the sealant material will be exposed immediately to pulsating, fluid flow which will exert forces both on the bond between the sealant material and the tissue and on the sealant material itself. The sealant material, therefore, must be able to withstand such forces immediately and for an extended period of time (that is, long enough for normal healing to take place). The materials of the present invention have demonstrated the ability to seal vascular tissue immediately upon polymerization without leakage when subjected to pressures in excess of 250 mm Hg, in excess of 300 mm Hg and even up to 500 mm Hg.

In connection with a damaged lung, parenchymal tissue and bronchiole tissue can be sealed with the methods and products of the invention. Parenchymal tissue repair typically involves sealing relatively small openings, whereas bronchiole tissue repair can involve sealing of substantial openings in tissue. The materials of the invention, immediately upon polymerization, can seal both parenchymal tissue injury and bronchiole stumps, which are exposed to immediate and pulsating pressures on the order of 45 mm Hg. Sealants used in repairing the lung also must last for periods of weeks to permit proper healing of lung tissue. Again, the materials and methods of the invention work to form seals which permit adequate healing without leakage.

The polymerizable proteins of the invention typically are applied as a viscous fluid. Particularly in connection with soft tissue and tissue with interstices, it is preferable to massage the viscous fluid onto the surface of the tissue to ensure adequate coverage of the surfaces of the tissue surrounding the openings being covered and to ensure covering the openings, thereby permitting solid, leak proof attachment of the covers to the tissue. The gel containing the polymerizable protein may include an initiator for polymerization. Preferably, the initiator is unable to cause polymerization of the polymerizable protein to any meaningful extent until activated by an initiator-activating agent (e.g. sodium persulfate activated by UV light).

The polymerizable protein may be derivatized to enhance solubilization at physiological conditions, as mentioned above. The polymerizable proteins also can be derivatized to enhance polymerization. Those skilled in the art know that collagen can be treated with a variety of moieties to achieve such improvements. See, for example, U.S. Pat. Nos. 5,104, 957 and 5,201,764, the disclosures of which are incorporated herein by reference. Suitable derivatives for enhancing solubilization are acylating agents and sulfonating agents.

The preferred polymerized protein is collagen derivatized with such agents. The solution, suspension, or viscous fluid containing the polymerizable protein may also contain native insoluble fibers such as insoluble collagen fibers. Such fibers can enhance the strength of the material, can effect cell growth on to the material and can effect the hemostatic properties of the material.

The preferred protein is collagen. The type of collagen useful to form a biologically compatible collagenous reaction product with the sealant properties of this invention is selected preferably from the following groups: purified Type I collagen, Type IV collagen and Type III collagen, or a combination of any of the foregoing. Preferred as a collagen starting material is purified Type I collagen. Type I collagen is ubiquitous and readily extracted from animal tissues such as dermis and tendon. Common sources are calf hide, tendon and steer hide. U.S. Pat. No. 4,969,912, "Human Collagen Processing and Autoimplant Use", describes unique methods to disperse and solubilize human tissue. The preferred source is derivatized as shown in the Examples.

A variety of collagen solubilization procedures that are well known in the art can be used to prepare soluble collagen solutions useful for the instant invention. Native collagen is liberated from non-collagen connective tissue constituents (lipids, sugars, proteins, etc.) and isolated after subjecting it to proteolytic enzymatic treatment by an enzyme other than collagenase. Suitable proteolytic enzymes include pronase and pepsin. The enzymatic treatment removes portions of the immunogenic non-helical portions of native collagen (telopeptide) and provides a monomeric collagen material which is soluble in dilute acidic aqueous media. A solution containing crude solubilized collagen is then subjected to a series of treatments to purify the soluble atelopeptide collagen from insoluble collagen, protease and non-collagen products resulting from the proteolytic enzymatic procedure. Conventional method for preparing pure, acid soluble, monomeric collagen solutions by dispersing and solubilizing native collagen are described, for example, in U.S. Pat. Nos. 3,934,852; 3,121,049; 3,131,130; 3,314,861; 3,530, 037; 3,949,073; 4,233,360 and 4,488,911. A method for preparing a collagen solution is provided in the examples that follow.

Suitable acylating agents for use in the instant invention include aliphatic, alicyclic and aromatic anhydrides or acid halides. Non-limiting examples of acylating agents include glutaric anhydride, succinic anhydride, lauric anhydride, diglycolic anhydride, methylsuccinic anhydride, methyl glutaric anhydride, dimethyl glutaric anhydride, succinyl chloride, glutaryl chloride, and lauryl chloride. These chemicals are available from Aldrich Chemical Company (Milwaukee, Wis.). Preferred acylating agent for use in the present invention is glutaric anhydride. An effective amount of an acylating agent is broadly from about 2.5 to 20% wt total collagen (an excess based upon moles required to react all free amines).

In addition, acylating agents having secondary reactive functionalities within their chemical structure are also useful for modifying protein monomers. Examples of secondary functionalities include by way of non-limiting examples: epoxy, cyano, halo, alkenyl, and alkynyl. Non-limiting examples of acylating agents bearing secondary functionalities include exo-3,6-epoxy-1,2,3,4-tetrahydrophthalic anhydride, methacrylic anhydride, 3,6-endoxo-3-methylhexahydrophthalic anhydride, and endo-3,6-endoxohexa hydrophthalic anhydride. Preferred as such acylating agents are exo-3,6-epoxy-1,2,3,4-tetrahydrophathalic anhydride and methacrylic anhydride.

Without being bound by theory, the secondary functionalities present in acylating agents can react covalently with amino acid residues under acylation conditions or during polymerization to enhance polymerization.

Useful sulfonating agents for the preparation of modified protein monomers of the present invention include aliphatic, alicyclic and aromatic sulfonic acids or sulfonyl halides. Non-limiting examples of sulfonating agents for use in the present invention include anthraquinone-1,5-disulfonic acid, 2-(chlorosulfonyl)-anthraquinone, 8-hydroxyquinoline sulfonic acid, 2-naphthalene-sulfonyl chloride, beta-styrene sulfonyl chloride and 2-acrylamido 2-methyl-1-propane sulfonic acid. These chemicals are available from Aldrich Chemical Company (Milwaukee, Wis.). The preferred sulfonating agent for preparing adhesive collagen materials is 3.5 dicarboxybenzenesulfonyl chloride. Such compounds, in non-toxic effective amounts, can be safely employed in collagen-based compounds for medical use as sealants. An effective amount of sulfonating agent is broadly from about 2.5 to 20% wt total collagen.

When a combination of a sulfonating agent and an acylating agent is used for preparation of modified collagen monomers, the amount of acylating agent and sulfonating agent in total, is preferably from about 2.0 to 20% wt total collagen.

Acylation of collagen is carried out at alkaline pH, for example, in the range from about 7.5 to 10.0, preferably from about 8.5 to 9.5, and more preferably at about pH 9.0. The acylation reaction can be monitored by the decrease in pH. The reaction is complete when pH remains stable. The reaction can also be monitored by removing aliquots and measuring the free amine concentration of precipitated, washed collagen product.

The acylation reaction should be complete in about 5 to 90 minutes, preferably from about 20 to 40 minutes. The reactions should be carried out at temperatures from about 4° C. to 37° C., preferably from about 4° C. to 25° C.

The reaction can be stopped by adjusting the pH to 12.0 for 2 minutes. This destroys residual, unreacted acylating agent. The modified collagen is then precipitated by reducing the pH using hydrochloric acid, acetic acid, nitric acid, sulfuric acid, or other acid.

The amount of acid must be sufficient to precipitate out the chemically derivatized collagen. Generally, precipitation occurs at a pH of between about 3.5 and 6.0, preferably between about 4.0 and 5.0.

The precipitate of reacted collagen which now contains substituent groups reacted with amine groups (primarily epsilon-amino groups), is recovered from the mixture using conventional techniques such as centrifugation or filtration. Centrifugation at about 3,000 to about 15,000 rpm for about 20 to 60 minutes, preferably from about 4,000 to 12,000 for about 20 to 30 minutes provides efficient recovery of the precipitate.

After recovery, the precipitate is washed with deionized water and subsequently dissolved in a physiological solution, e.g., phosphate buffer (0.1M) at pH 7.2. It is often necessary to adjust the pH to the preferable range of 8.2 to 8.5 by addition of sodium hydroxide solution.

Following dissolution of the precipitate, the solution is generally filtered by conventional filtering means, i.e., a 5 micron filter, and then centrifuged to remove air bubbles. At this point, the resulting solution containing chemically modified collagen monomers exhibits a viscous consistency and varying degrees of transparency and clarity depending on the extent of acylation and on the state of solubility of the starting collagen material.

The extent of acylation determines the biological stability of the resultant sealant. Complete acylation, reaction with all available free amines, produces a collagen composition with desirable solubility. In some cases the acylation reaction produces desirable amounts of moieties that are helpful in adhering the material to tissue. The biological stability of resultant sealants, however, is affected by controlling the extent of acylation. The greater the acylation, the less stable is the polymerizable material, generally. The extent of acylation may be modulated by varying the amount of acylation agent, the pH, the temperature and the time of the reaction. In addition, the method of addition of the acylating agents will affect the reaction. Reactions are generally slower if the acylating agent is added as a solid or powder rather than as a solution.

The chemically modified collagen solution thus obtained is subsequently subjected to polymerization or crosslinking conditions to produce the polymerized collagen composition of the present invention. Polymerization may be carried out using irradiation, e.g., UV, gamma, or fluorescent light. UV irradiation may be accomplished in the short wave length range using a standard 254 nm source of UV. It also preferably is accomplished using a broader range light source such as 250–550 nm light source (EFOS, Model Novacure, 100 ss+ Missisauga, Ontario, Calif.).

Excess UV exposure will begin to depolymerize the collagen polymers. Polymerization using gamma irradiation can be done using from 0.5 to 2.5 Mrads. Excess gamma exposure will also depolymerize collagen polymers. Polymerization in the presence of oxygen requires the addition of an initiator to the fluid prior to exposure. Non-limiting examples of initiators include sodium persulfate, sodium thiosulfate, ferrous chloride tetrahydrate, sodium bisulfite and oxidative enzymes such as peroxidase or catechol oxidase. When initiators are employed, polymerization occurs in 10 seconds to 3 or more minutes, preferred ranges depending upon the polymer selected and tissue being treated. Preferred as a polymerizing agent is UV irradiation.

Collagen products containing methacrylic acid polymerize spontaneously in air. This polymerization can be accelerated under UV irradiation in the absence of oxygen.

The foregoing discussion is meant to be a general teaching relating to the preparation of polymerizable collagen. The most preferred embodiments are detailed in the examples below. In general, the exact composition will depend upon the particular tissue being treated and the particular polymer selected. In connection with lung tissue, a concentration of derivatized collagen of between 15 and 50 mg/ml is preferred, most preferably the concentration being between 20 and 25 mg/ml. For vascular applications, the concentration of collagen is preferably between 20 mg/ml to 90 mg/ml, most preferably between 40 mg/ml to 80 mg/ml. In general, collagen concentrations will beneficially range between 5 mg/ml (5%) to 100 mg/ml (10%).

In order to enhance the flexibility of the polymerized covering, it may be advantageous to add a conventional plasticizer to the viscous fluid, such as glycerol, sorbitol, manitol, erythritol, xylitol, polyethylene glycol etc.

Compositions can include the addition of collagen fibers, preferably Avitene obtained from MedChem, Inc., a subsidiary of C.R. Bard, Woburn, Mass. These fibers are important for their tensile strength in such applications. They may be short (less than 850 microns), long (greater than 850 microns and less than 2 millimeters) or mixed short and long fibers. Their concentration is between 10 and 30 mg/ml and preferably 15–25 mg/ml.

In preferred embodiments, the persulfate is present at between 0.01M final concentration and 0.2M final concentration. Useful levels include 0.3M stock—at 1.6 to 8.0 ml collagen (0.05M final), 0.5M stock—at 1.6 to 8.0 ml collagen (0.08M final) and 0.7M stock—at 1.6 to 8.0 ml collagen (0.116M final). Stock conditions are 0.1M phosphate buffer, pH=8.2–8.5. It is important to stock the persulfate in buffer solution to avoid adverse change to the pH of the collagen material when added to the collagen material. The final preparation preferably has a pH of 6.0–9.0, preferably 8.2–8.5. Thus, the collagen and persulfate may be mixed together immediately prior to application (with pH adjustment occurring if persulfate is added in water and not in a buffered solution). Alternatively, the collagen material may be applied to the tissue and then overcoated with persulfate, preferably in buffered solution. For vascular coverings, the material is in the form of a viscous fluid and is applied in a 1–2 mm even overcoat, after which the material is irradiated. For the lung application, the material is applied in a thinner coating and is massaged into the tissue surfaces before light polymerization.

The preferred light source is a broad band from 250 to 550 nm (Novacure, 100 ss+). For blood vessel applications, the intensity×time ranges from 2500 mW×15 seconds to 4500 mW×45 seconds and preferably 3000 mW×15 seconds to 4500 mW×30 seconds. For the lung application, the intensity×time preferably is 2500 mW×75 seconds to 4500 mW×180 seconds, more preferably 2500 mW×15 seconds to 4500 mW×45 seconds.

The polymerizable proteins described above form a strong seal over damaged tissue when subjected to polymerization or crosslinking conditions. The strength of the seal can be enhanced further by applying a primer solution to the tissue prior to applying the polymerizable protein. Often the surface of a damaged tissue to which the polymerizable protein is to be applied may be coated with various naturally-occurring proteins and/or blood, the presence of which may influence the intimate contact between the sealant and the tissue surface. Simple flushing of the tissue surface with saline solution may not remove or displace these substances. It was found according to one aspect of the invention that a tissue surface coated with various naturally-occurring proteins and/or blood can be pre-treated with a primer solution in order to enhance the contact between the tissue and the polymerizable proteins. It is believed that the primer enhances this interaction by diluting or displacing the proteins and/or blood.

A primer, as used herein, is a biologically compatible adhesive protein solution. Proteins useful as primers include collagen, albumin, gelatin, elastin, and fibrinogen. A preferred primer, is a dilute solution of collagen in 0.1M phosphate buffer. The collagen concentration is 1 to 10 g/ml, more preferably 4 to 8 mg/ml. The pH of the solution is 6.0 to 9.0, more preferably 8.2 to 8.5. Optionally the solution may be supplied in a plastic syringe.

The primer may be used in various combinations with polymerizable proteins of the invention. For instance, a collagen primer may be used with polymerizable proteins that are collagen, elastin, fibrinogen, etc. The primer may also be a combination of adhesive proteins. The primer may be, for example, a combination of collagen and elastin.

The primer is applied to the tissue prior to the polymerizable protein. First the tissue surface is blotted with a sponge to remove excess proteins and/or blood and then the primer is applied, preferably, using a syringe. The primer may be gently rubbed in to the surface and the excess primer removed. The polymerizable protein is added to the primer coated surface while the primer is still moist. A preferred embodiment for sealing a tissue using a primer is set forth in more detail in the examples below.

The primer may be used with any protein based adhesive. In a preferred embodiment, the primer is used with the polymerizable proteins of the invention. The primer, however, may be used with any protein based adhesive known in the art, such as those disclosed in the background of the invention. For example, modified collagen-based adhesives, and fibrin glues are well known protein based adhesives.

The working Examples set forth below are intended to illustrate the invention, without limiting the scope thereof.

EXAMPLES

Example 1

Preparation of Polymerizable Protein Sealant

1. Preparation of a Collagen Gel

A. Extraction and Purification of Collagen

Collagen was prepared from powdered bovine corium. This powder is subsequently heat sterilized to produce Avitene (MedChem Products, Inc., Woburn, Mass.). The powder is primarily composed of type I collagen.

Powdered bovine corium was suspended in 0.5M acetic acid at 3 grams per liter. Pepsin (Sigma Chemical Co., 1:60,000) was added at 3% (wt/wt Avitene powder) and the suspension mixed at room temperature for 48–72 hours using a lightning mixer. An additional 1% of pepsin (wt. per weight of Avitene powder) was added to complete the digestive reaction. Following this addition, the suspension was mixed for another 24 hours. Extent of digestion is monitored using high pressure chromatography to determine the content of monomolecular collagen. The second addition of pepsin is not necessary if results from HPLC indicate that the digestion is complete after the first pepsin digestion.

The digested collagen mixture was filtered through a coarse filter or centrifuged at 9,000 rpm to remove undigested material. The clarified suspension was then diafiltered using 5 volumes of 0.1M acetic acid to remove most of the soluble, low molecular weight pepsin. Dialysis was conducted using a hollow fiber cartridge with a 100,000 MW cut-off. Following dialysis, Type I collagen was purified by the addition of NaCl (sodium chloride) to a final concentration of 0.85M. The suspension was mixed for at least two hours and the collagen precipitate recovered by centrifugation for 30 minutes at 9,000 rpm. The pellet was redissolved in 0.1M acetic acid to a concentration of approximately 3 mg/ml (0.3%) and filtered through a series of filters, i.e., approximately $1\mu$ prefilter, $0.4\mu$ filter and finally sterile filtration through a $0.22\mu$ filter. This purified Type I collagen suspension was then used for chemical derivatization.

The sterile filtered collagen suspension was pH adjusted to 9.0 using 10N and 1N NaOH. Glutaric anhydride was added at 10% (weight of collagen) and mixed for 30 minutes while maintaining the pH at about 9.0. Glutaric anhydride reacts with deprotonated $\epsilon$- and terminal free amines resulting in the addition of a carboxyl group to the amine. Derivatized collagen was recovered by reducing the suspension to its new pKa of approximately 4.3. This was accomplished using 6N and 1N Hcl. The precipitate was collected by centrifugation for 20 minutes at 9,000 rpm.

The recovered derivatized-collagen pellet was dissolved in 0.1M phosphate buffer (pH 8.2–8.5) to which was added 1N NaOH, if necessary, to adjust the final pH to about 8.2–8.5. The concentration ranges for various formulations were from 18 mg/ml to 90 mg/ml and dynamic viscosities ranged from about 50,000 cps to more than 200,000 cps. The final concentration depends on application. However, the preferred concentration appears to be about 50 mg/ml and exhibits a dynamic viscosity of about 80,000 cps.

For some applications, i.e., sealing vascular fluid leaks, the strength of the polymerized collagen sealant was enhanced by adding Avitene fibers at a concentration of 5–20 mg/ml. The preferred concentration depends on application but is generally about 10 mg/ml.

2. Preparation of the Polymerizable Protein Sealant from the Collagen Gel

The polymerizable protein sealant was prepared for application by mixing 0.8 ml of collagen gel with 0.16 ml of a 0.7M solution of sodium persulfate in 0.1M phosphate buffer to produce a final solution having a pH 8.2–8.5. The solutions were mixed in two 1 ml syringes connected by a syringe adapter. A first 1 ml syringe was filled with 0.8 ml collagen gel and a second 1 ml syringe was filled with 0.166 ml of sodium persulfate solution. The two syringes were connected by a syringe adapter and the solutions were mixed by transferring the two solutions back and forth between the two syringes 40 to 50 times over a 25 to 30 second time interval. Care was taken to avoid introducing air bubbles into the mixture. The solutions, however, may be mixed by any traditional technique for combining solutions, such as in a test tube with a spatula. The syringe method, however, is preferred because of its ease of handling and ability to avoid air bubbles as well as its sterility. The final pH of the sealant was between 8.2 and 8.5. The sealant was incubated in a capped 1 ml syringe for 5 to 10 minutes at room temperature before application to the tissue. Incubation temperatures up to 35° C. may be used.

Example 2

Process for Sealing Lung Tissue with Polymerizable Protein Sealant

1. Application of the Polymerizable Protein Sealant to a Deflated Lung

The surface tissue of a deflated lung was thoroughly dried with gauze. Approximately 0.2 ml of sealant was applied to the tissue surface and gently rubbed into the exposed lung tissue, as well as 5 mm of surrounding pleura for 30 seconds, with a dry gloved fingertip and/or a spatula. A larger volume of sealant may be applied to the tissue for the treatment of larger surface areas. More sealant was then applied over the exposed lung tissue and pleura already having an initial coat of sealant, to produce a 1–2 mm layer of sealant over the tissue and pleura. Care was taken to avoid generating bubbles at the site.

2. Polymerization of the Polymerizable Protein Sealant on the Deflated Lung

The sealant was polymerized, or "cured" by exposure to ultraviolet-A light delivered through a liquid-filled light guide by an EFOS Novacure unit. The ultraviolet light intensity used was in the range of 3000 mW/cm$^2$. The exposure time was 135 seconds but the exposure time may range from 1 to 300 seconds. The light guide distance was 3 inches but the light guide distance may be anywhere between 1 and 3 inches, depending on the surface area to be exposed as well as the exposure time. Light exposure was repeated over all areas to which sealant was applied in order to ensure that the sealant was evenly polymerized.

Example 3

In Vivo and Ex Vivo Analysis of the Polymerizable Protein Sealant as a Hemostat and a Lung Sealant.

1. Analysis of the Polymerizable Protein Sealant as Hemostat in an Isolated Porcine Abdominal Aorta An abdominal aorta mounted in line with a pressurized reservoir of saline was punctured with an eighteen gauge needle. The presence of the hole was confirmed by applying pressurized saline and observing leakage at the hole site. The surface around the hole was blotted and the polymerizable protein sealant was applied over the hole and the surrounding area. The sealant was gently rubbed into the tissue area surrounding and over the hole for thirty seconds, with a dry gloved fingertip and/or a spatula. Additional sealant was applied to produce a 1–2 mm layer of sealant over the entire area. The sealant was cured for fifteen seconds using an ultraviolet light. The vessel was then pressurized up to 300 mm of mercury by opening the saline reservoir. Although the vessel distended approximately 30 percent, the sealant held in place at least up to 300 mm of mercury. Other in vitro tests have shown that the sealant is capable of sealing tissues under normal blood pressure for extended periods of time.

2. Analysis of the Polymerizable Protein Sealant as a Hemostat in Situ

An abdominal aorta of a pig, in situ, was pierced with an eighteen gauge needle. Temporary hemostatis was achieved with proximal and distal clamps. The surface surrounding the hole was blotted and the polymerizable protein sealant was applied with a spatula and gently rubbed into the exposed tissue surrounding the hole and over the hole for thirty seconds. An additional layer of sealant was applied, to produce a 1–2 mm layer of sealant over the tissue. The tissue was cured for fifteen seconds using ultraviolet light. The clamps were removed and hemostatis was achieved.

3. Analysis of the Polymerizable Protein Sealant in an Inflated Porcine Lung

The tip of an inflated porcine lung lobe was removed to expose a bronchus of approximately 1 mm in diameter. The surface was blotted and the polymerizable protein sealant was applied over the exposed tissue as well as at least 5 mm of surrounding pleura. The sealant was gently rubbed into the exposed lung tissue and pleura for thirty seconds, with a dry gloved fingertip and/or a spatula. Additional sealant was applied to produce a 1–2 mm layer of sealant over the entire exposed area. The sealant was cured for fifteen seconds with an ultraviolet light. Absence of an air leak was verified by pressurizing the lung up to 60 mm of mercury, which corresponds to 80 cm of water.

4. Analysis of the Polymerizable Protein Sealant as an in Vivo Canine Lung Sealant An upper lobe of a canine lung was severed to expose a tissue surface area. The sealant was applied as described above and cured with ultraviolet light for fifteen seconds. The absence of an air leak was verified by submerging the lung and increasing the expiatory pressure to approximately 20 cms of water. The absence of a leak was again verified after twenty-four hours.

5. Analysis of the Polymerizable Protein Sealant as an in Vivo Porcine Lung Sealant A lobe of porcine lung tissue was severed to reveal a tissue surface area. The sealant was applied as described above and was cured with ultraviolet light for fifteen seconds. The absence of an air leak was verified by dripping saline solution over the sealant.

Example 4

Preparation and Analysis of a Primer/Polymerizable Protein Sealant as a Hemostat 1. Preparation of a Primer/Polymerizable Protein Sealant Collagen was prepared as described in Example 1 above. The collagen was then diluted with 0.1M phosphate buffer pH 8.2 to produce a concentration of 4 to 8 mg/ml. The pH of the solution was adjusted to a value of 8.35 using 0.1N NaOH. The dilute collagen solution was loaded into a plastic syringe for administration.

2. Analysis of a Primer/Polymerizable Protein Sealant as a Hemostat

The carotid or femoral artery of a heparinized dog was clamped proximally and distally. A 15 mm longitudinal arteriotomy was created, then repaired with a continuous suture of 6-0 polypropylene, leaving gaps approximately 3.5 mm long between stitches. The distal clamp was released momentarily to confirm that the suture line was not hemostatic. Excess blood was rinsed away with saline, and the artery surface blotted with a gauze sponge. Primer was applied using a syringe to all surfaces to which sealant application was anticipated. The primer was gently rubbed into the surface using the blunt tip of the syringe. Excess primer was blotted so that the tissue surface is left slightly moist, or glistening, but not dry. The polymerizable protein solution was then applied to the prepared site to form a 1–2 mm layer and cured by ultraviolet light. The artery clamps were released, distally then proximally, and hemostasis was achieved.

The use of primer resulted in superior hemostasis results. Immediate hemostasis was achieved in 3 of 6 arteriotomies without the primer, and in 6 of 7 arteriotomies with the use of primer.

Each of the foregoing patents, patent applications and references is herein incorporated by reference in its entirety. Having described the presently preferred embodiments, in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

We claim:

1. A method for sealing a fluid leak in a tissue, comprising:

applying on the tissue a polymerizable protein to form a covering for an opening that creates a fluid leak in the tissue, wherein the tissue is selected from the group consisting of a tissue which is subjected to pulsating fluid pressures and a tissue having an opening that forms a substantial gap; and exposing the covering to an initiator so as to polymerize the covering in situ, so as to attach the covering to the tissue and so as to seal the opening from fluid leakage.

2. The method of claim 1, wherein the polymerization occurs in less than thirty seconds.

3. The method of claim 2, wherein the polymerization is carried out in a viscous fluid maintained at between pH 7.3 and 7.5.

4. The method of claim 1, wherein the polymerization occurs in between about ten and thirty seconds.

5. The method of claim 1, wherein the polymerization occurs in about fifteen seconds.

6. The method of claim 1, wherein the polymerizable protein is applied on the tissue as a viscous fluid and the viscous fluid includes an initiator.

7. The method of claim 6, wherein the initiator is selected from the group consisting of sodium persulfate, sodium thiosulfate, ferrous chloride tetrahydrate, sodium bisulfite, and an oxidative enzyme.

8. The method of claim 7, wherein the initiator is sodium persulfate and the sodium persulfate is present in an amount ranging from 0.01M to 0.2M, final concentration.

9. The method of any of claims 1–8, wherein the polymerizable protein is derivatized and the polymerizable protein is selected from the group consisting of collagen, albumin, gelatin, elastin, and fibrinogen.

10. The method of any of claims 1–8, wherein the polymerizable protein is applied as a viscous fluid and comprises derivatized collagen and insoluble collagen.

11. The method of claim 6, wherein a plasticizer is added to said viscous fluid.

12. The method of claim 11, wherein said plasticizer is selected from the group consisting of glycerol, sorbitol, manitol, erythritol, and xylitol.

13. The method of claim 9, wherein the polymerizable protein is collagen and said collagen is derivatized by reacting with an agent selected from the group consisting of acylating agents and sulfonating agents.

14. The method of claim 9, wherein the tissue is selected from the group consisting of blood vessel tissue, lung tissue, bowel tissue, and dura tissue.

15. The method of any of claims 1–8, wherein the covering is polymerized in situ using irradiation.

16. The method of claim 15, wherein the irradiation is a light band having wavelengths of between 250 and 450 nm.

* * * * *